July 15, 1975 A. BARBERET ET AL Plant Pat 3,743
CARNATION PLANT
Filed April 25, 1974
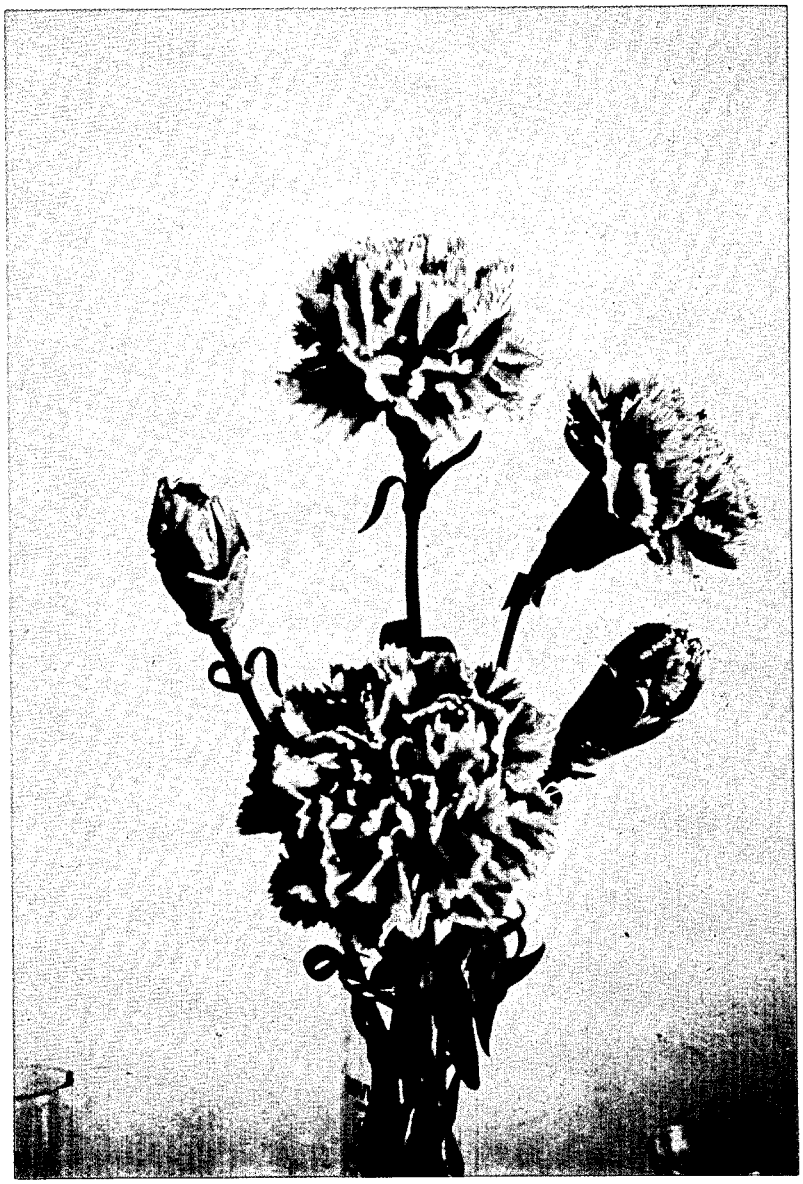

United States Patent

Plant Pat. 3,743

Patented July 15, 1975

3,743

CARNATION PLANT

Alexandre Barberet and Henri Blanc, La Londe, France, assignors to Laboratoire de Physiologie Vegetale de La Londe, Barberet & Blanc, La Londe-les-Maures, France Filed Apr. 25, 1974, Ser. No. 463,970

Int. Cl. A01h *5/00*

U.S. Cl. Plt.—70 1 Claim

ABSTRACT OF THE DISCLOSURE

A new variety of carnation plant of the "American" type, particularly suitable for cut flowers production, distinguished by the unusual red coloring of its blossoms, which is of intense garnet color near the center of the flower, shading toward the ends of the petals where the margins become almost clear of color, and by its very long and strong flower stems.

*Background of the Invention*

This new carnation plant originated at La Londe, France, as a seedling derived by a crossing of carnation varieties selected from breeding stock maintained in our laboratories at La Londe, France, with the object of developing improved carnation plants for the production of cut flowers. This new plant was discovered by us in 1970 and observed to have an unusually attractive flower of a deep red color carried on long, strong stems and particularly suitable for the cut flower market. Asexual propagation of this new plant by means of cuttings has been carried on under our direction through several generations at La Londe, France, and the distinctive characteristics of this plant have been found to hold true from generation to generation and appear to be firmly fixed.

*Description of the Drawing*

Our new variety of carnation plant is illustrated by the accompanying full color photographic drawing which shows buds and fully opened blossoms and which shows the flower coloration as nearly true as it is reasonably possible to obtain by means of conventional photographic procedures.

*Description of the New Plant*

The following is a detailed description of our new variety of carnation plant based upon observations made in January 1974 of plants set out in July 1973 and grown under conventional greenhouse practices, the color designations being according to the R.H.S. Colour Chart published by the Royal Horticultural Society at London, England, in collaboration with the British Colour Council.

THE PLANT

Origin: Seedling.
Parentage:
- Seed parent—8G4 (unpatented).
- Pollen parent—332G (unpatented)
  - These plants are maintained in our laboratories at La Londe, France, and are identified in our permanent records by the above designations.

Classification:
- Botanic—Dianthus Caryophyllus.
- Commercial—Greenhouse carnation for cut flowers.

Form: Bush. As Sim types.
Height: The plant flowers at a height of 101 cm. at an age of about 6 months.
Growth: Vigorous and erect.
Branching: Normal, the principal stem having 2 or 3 flowering shoots or branches from the lower one-third of its length.

Foliage: Quantity—sparse.
- Leaf—Size: Average—6 to 14 cm., average 10 cm. Shape: Lanceolate. Margin—entire.
- Texture: Smooth.
- Color: Upper side—Greyed Green 189B. Under side—Same.
- Ribs: One central rib most visible at under side.
- Petiole: None. Leaf is amplexicaul.

THE BUD

Size: Medium, about 22 mm. in diameter.
Form: Generally ovoid; conical at beginning becoming ovoid at opening of sepals.
Opening: Bud opens slowly.
Calyx: Size—large.
- Shape: Pear shaped, becoming cylindrical and wide mouthed as petals begin to unfurl. Calyx very rarely splits.
- Aspect: Smooth.

Sepals: Five in number, generally oval in shape with mucronate tip.
- Condition: Upstanding. Tip ends curl back as flower opens.
- Color: Inside—Pale Green. Outside—Light Green.

Peduncle: Rigid and upright.

THE FLOWER

Blooming Habit: Continuous and profuse.
Size of Bloom: Medium. Average diameter—7.3 cm. Average depth—5.2 cm.
Borne: Singly.
Shape: High center at first opening, becoming dome-shaped as blossom matures.
Petalage: Number of petals—60 to 74, averaging about 66.
- Arrangement: More or less imbricated.
- Form: Fan shaped with frilled end margins.
- Color: Outer and inside petals—53A to 53B at center of petals body, fading to 56A near margins and becoming almost clear white at frilled ends of petals. Reverse side—53D to 54A at center of petal body, fading to 56B near margins of petals and becoming off-white at tip end edges.
- Appearance: Satiny.

Petaloids: Number—average 5.
- Size: Half the size of the flower petals.
- Color: Same as petals.

Peduncle: Flowering stem—Upright and rigid with length of about 61 cm.
Persistence: Flowers hang on and dry.
Fragrance: Perceptible.
Disease Resistance: Resistant to all common carnation diseases prevalent in areas where carnations are grown.
Lasting Quality:
- On plant—15 days.
- As cut flower—10 days.

REPRODUCTIVE ORGANS

Stamens: Filaments—3 cm. long. Color—White.
- Anthers: None in wintertime.

Pistils: Number—3.
- Length of Style: 3.5 cm.
- Stigmas: Color—Flushed with crimson at maturity.

Ovaries: Superior, cone shaped, whitish at base, light green medially and ocre yellow at top.
Fruit: Fertile, a little in summer.
- Shape: Pear-shaped.
- Color: Green and ocherous.

Our new variety of carnation plant is particularly distinguished by the deep red coloring of its flowers which have petals with frilled tip-end margins of pale almost white color and which are borne on long, strong stems. The flower has a closed calyx, rarely splitting, and the plant has such an aptitude for continuous production of blossoms as to have considerable commercial merit for the cut flower market.

We claim:

1. A new and distinct variety of carnation plant, substantially as herein shown and described, characterized by its high productivity of flowers of deep red color, the petals of which have frilled tip end margins of clear white.

No references cited.

ROBERT E. BAGWILL, Primary Examiner